United States Patent
Cha

(10) Patent No.: US 10,342,931 B2
(45) Date of Patent: Jul. 9, 2019

(54) OPTICALLY INDUCED INJECTION DEVICE

(71) Applicants: PUSAN NATIONAL UNIVERSITY INDUSTRY-UNIVERSITY COOPERATION FOUNDATION, Basan (KR); PUSAN NATIONAL UNIVERSITY HOSPITAL, Busan (KR)

(72) Inventor: Wonjae Cha, Busan (KR)

(73) Assignees: PUSAN NATIONAL UNIVERSITY INDUSTRY-UNIVERSITY COOPERATION FOUNDATION, Busan (KR); PUSAN NATIONAL UNIVERSITY HOSPITAL, Busan (KR)

( * ) Notice: Subject to any disclaimer, the term of this patent is extended or adjusted under 35 U.S.C. 154(b) by 0 days.

(21) Appl. No.: 15/536,419

(22) PCT Filed: Aug. 18, 2016

(86) PCT No.: PCT/KR2016/009067
§ 371 (c)(1),
(2) Date: Jun. 15, 2017

(87) PCT Pub. No.: WO2017/039193
PCT Pub. Date: Mar. 9, 2017

(65) Prior Publication Data
US 2018/0185591 A1 Jul. 5, 2018

(30) Foreign Application Priority Data
Sep. 3, 2015 (KR) .......................... 10-2015-0124856

(51) Int. Cl.
*A61M 5/42* (2006.01)
*A61M 5/31* (2006.01)
(Continued)

(52) U.S. Cl.
CPC ........... *A61M 5/427* (2013.01); *A61B 1/0676* (2013.01); *A61B 1/267* (2013.01); *A61M 5/31* (2013.01); *A61M 5/42* (2013.01); *A61B 5/0084* (2013.01)

(58) Field of Classification Search
CPC ..... A61B 1/0676; A61B 1/267; A61B 5/0084; A61M 5/31; A61M 5/42; A61M 5/427
See application file for complete search history.

(56) References Cited

U.S. PATENT DOCUMENTS

| | | |
|---|---|---|
| 4,624,243 A | 11/1986 | Lowery et al. |
| 5,183,031 A | 2/1993 | Rossoff |
| 2014/0135630 A1 | 5/2014 | Berndt |

FOREIGN PATENT DOCUMENTS

| | | |
|---|---|---|
| JP | 2000-312719 A | 11/2000 |
| JP | 2008-539942 A | 11/2008 |

(Continued)

OTHER PUBLICATIONS

Chhetri, et al., "Percutaneous Injection Laryngoplasty," *The Laryngoscope*, 124:742-745, (2014).
(Continued)

*Primary Examiner* — Imani N Hayman
(74) *Attorney, Agent, or Firm* — Alston & Bird LLP

(57) ABSTRACT

An optically induced injection device is provided. The optically induced injection device includes: an injection needle, a light generator providing light to an affected area, a first optical cable which is disposed in the injection needle and through which the light passes, and an injection unit disposed in the injection needle and providing an injection solution to the affected area while the light is provided to the affected area.

16 Claims, 11 Drawing Sheets

(51) Int. Cl.
 *A61B 1/06* (2006.01)
 *A61B 1/267* (2006.01)
 *A61B 5/00* (2006.01)

(56) References Cited

FOREIGN PATENT DOCUMENTS

| JP | 2012-515603 A | 7/2012 |
| KR | 10-0531163 B1 | 11/2005 |
| WO | WO 2017-039193 A1 | 11/2000 |

OTHER PUBLICATIONS

Cha, et al., "Development of a Device for Real-Time Light-Guided Vocal Fold Injection: A Preliminary Report," *The Laryngoscope*, 126:936-940, (2016).
PCT International Search Report for application PCT/KR2016/009067 dated Dec. 5, 2016.

OPTICALLY INDUCED INJECTION DEVICE

CROSS REFERENCE TO RELATED APPLICATIONS

This application is a 371 National Stage Application of PCT/KR2016/009067, filed Aug. 18, 2016, which claims priority to Korean Application No. 10-2015-0124856, filed Sep. 3, 2015, the contents of all of which are incorporated herein by reference in their entirety.

BACKGROUND

1. Technical Field

Exemplary embodiments of the present disclosure relate to an optically induced injection device for use in transcutaneous vocal fold injection.

2. Description of the Related Art

Transoral injection is performed under general anesthesia or partial anesthesia, but, recently, has been mostly adapted under partial anesthesia in the outpatient department. This procedure is a method in which mucosal anesthesia was performed throughout oral cavity, alveolar, hypopharynx and larynx, and then a drug is directly injected into the upper edge of vocal folds through the oral cavity while monitoring the vocal folds using a transoral laryngeal endoscope. This method is widely used, and has an advantage of determining the exact position of vocal folds while directly seeing the vocal folds. However, since this method requires sufficient mucosal anesthesia as compared with other methods and requires to allow the vocal folds of a patient to be directly manipulated in a state where the patient is conscious, this method requires anesthesia to such a degree of blocking laryngeal reflection as well as zone reflection.

In particular, the laryngeal side of epiglottis requires a caution because it is sensitive to laryngeal reflection, is a site having a lot of contact with instruments during the procedure, and stimulates a patient during the procedure to cause an emergency due to laryngeal spasm or vascovagal syncope. Further, Many practitioners who have started vocal fold injection experience a patient with lidocaine toxicity during mucosal anesthesia. When an anesthetic is applied to vocal folds to such a degree of blocking laryngeal reflection, a large amount of anesthetic is absorbed into systemic blood stream through airway mucosa or lung, and elderly patients or patients with liver dysfunction easily reach the addiction of anesthetic to be accompanied by dizziness, nausea, abnormal pronunciation, decreased vision, tonic-clonic seizure, and the like, and, if severe, to lead to respiratory failure and deterioration in consciousness.

Further, since the anesthetic passes through vocal fold mucosa during the procedure, suction due to bleeding may occur. During the procedure, as a technical problem, there is a disadvantage that, at the time of injecting a drug into vocal folds, although the drug can be relatively accurately injected while observing the tip of an injection needle, it is difficult to conduct a fundamental manipulation because of using a long instrument, and, particularly, a possibility of injecting the drug into a wrong position increases when zone reflection is severe.

SUMMARY

Exemplary embodiments of the present disclosure provide an optically induced injection device which can simultaneously provide light and an injection solution into an affected area.

Additional advantages, subjects, and features of the present disclosure will be set forth in part in the description which follows and in part will become apparent to those having ordinary skill in the art upon examination of the following or may be learned from practice of the present disclosure.

According to an exemplary embodiment of the present disclosure, there is provided an optically induced injection device, including: an injection needle; a light generator providing light to an affected area; a first optical cable which is disposed in the injection needle and through which the light passes; and an injection unit disposed in the injection needle and providing an injection solution to the affected area while the light is provided to the affected area.

The injection needle may have an outer diameter of 0.305 mm to 1.270 mm.

The injection needle may have an inner diameter of 0.140 mm to 0.838 mm.

The first optical cable may have a diameter of 10 µm to 200 µm.

An injection needle tip formed at one end of the injection needle may further protrude compared to a first optical cable terminal formed at a position corresponding to the one end of the injection needle.

The optically induced injection device may further include: a body connecting the injection needle and the light generator.

The optically induced injection device may further include: a second optical cable connecting the light generator and the body and providing the light generated from the light generator to the injection needle.

The first optical cable and the second optical cable may be disposed to be spaced apart from each other in the body.

The optically induced injection device may further include: an injection needle connector disposed to the other end of the injection needle and connecting the injection needle and the body, wherein the injection needle connector is detachable from the body.

The optically induced injection device may further include: a reflective film disposed on the inner surface of the injection needle connector and reflecting the light into the injection needle.

The optically induced injection device may further include: a fixing unit disposed on the lateral surface of the body and fixing the injection needle connector to the body.

The first optical cable may be connected with the body, and, when the injection needle connector is detached from the body to allow the injection needle to be detached from the body, the first optical cable disposed in the injection needle may be separated from the injection needle.

According to an exemplary embodiment of the present disclosure, there is provided an optically induced injection device, including: a housing; a light generator connected with the housing and providing light to the housing; a syringe connected with the housing and providing an injection solution to the housing; and an injection needle connected with the housing and providing the injection solution to an affected area while the light is provided to the affected area.

The light may be a laser.

The housing may reflect the light into the housing.

The optically induced injection device may further include: a total reflection coating film disposed on the inner surface of the housing to totally reflect the light.

The light generator may be disposed on the lateral surface of the housing, and the light may be applied into the housing.

The optically induced injection device may further include: a light-transmitting film covering an opening through which the light is applied.

The injection needle may reflect the light into the injection needle.

The optically induced injection device may further include: a syringe connector connecting the housing and the syringe, wherein the syringe is detachable from the syringe connector.

Other specific details of the present disclosure are included in the detailed description and the drawings.

According to the optically induced injection device of the present disclosure, the injection accuracy of an injection solution can be improved in the transcutaneous vocal fold injection. Thus, it is possible to ensure the stability and easiness of procedure through advantages such as reduction of anesthesia time and procedure time, fewer complications, and good patient compliance.

The effects of the present disclosure are not limited to the above-described effects, and other unmentioned effects will be clearly understood to those skilled in the art from the description of claims.

DETAILED DESCRIPTION OF THE EMBODIMENTS

Figure 1:
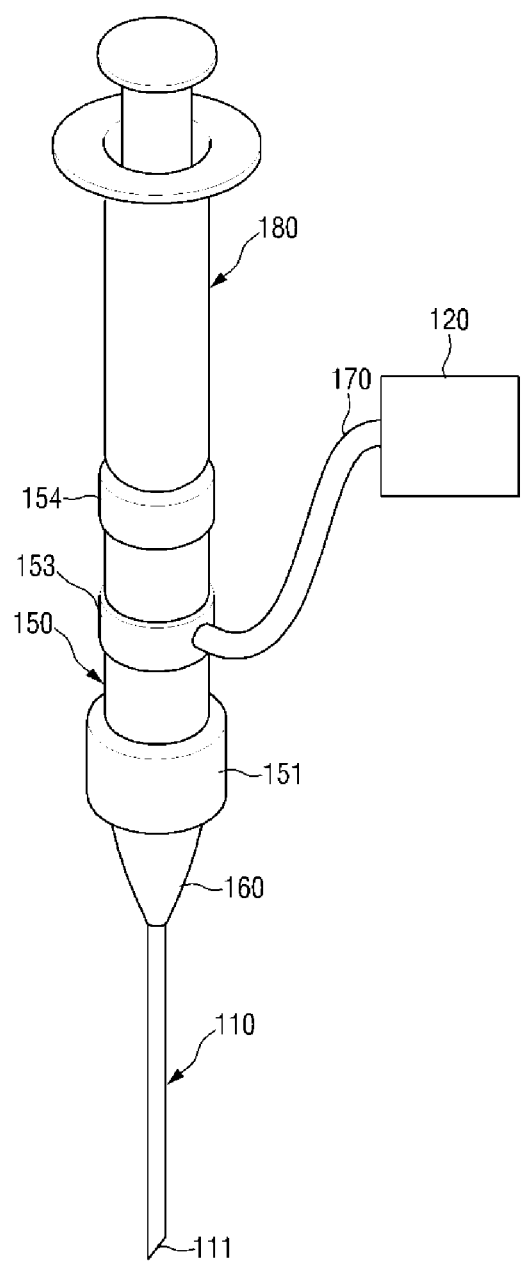
FIG. 1 is a perspective view of an optically induced injection device according to an exemplary embodiment of the present disclosure.

Advantages and features of the present disclosure and methods of accomplishing the same may be understood more readily by reference to the following detailed description of preferred embodiments and the accompanying drawings. The present disclosure may, however, be embodied in many different forms and should not be construed as being limited to the embodiments set forth herein. Rather, these embodiments are provided so that this disclosure will be thorough and complete and will fully convey the present disclosure to those skilled in the art, and the present disclosure will only be defined by the appended claims. In the drawings, the thickness of layers and regions are exaggerated for clarity.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure.

The terms used herein is for the purpose of illustrating embodiments, and is not intended to restrict the present disclosure. In the description, a singular expression may include a plural expression unless specially described unless otherwise specified. The term "comprises" and/or "comprising" used in the description means that one or more other components, steps, operation and/or existence or addition of elements are not excluded in addition to the described components, steps, operation and/or elements.

Unless defined otherwise, all technical and scientific terms used herein have the same meaning as commonly understood by one of ordinary skill in the art to which this present disclosure belongs. It is noted that the use of any and all examples, or exemplary terms provided herein is intended merely to better illuminate the present disclosure and is not a limitation on the scope of the present disclosure unless otherwise specified. Further, unless defined otherwise, all terms defined in generally used dictionaries may not be overly interpreted.

Hereinafter, an optically induced injection device according to an exemplary embodiment of the present disclosure will be described with reference to FIG. 1 to FIG. 5.

Figure 2:
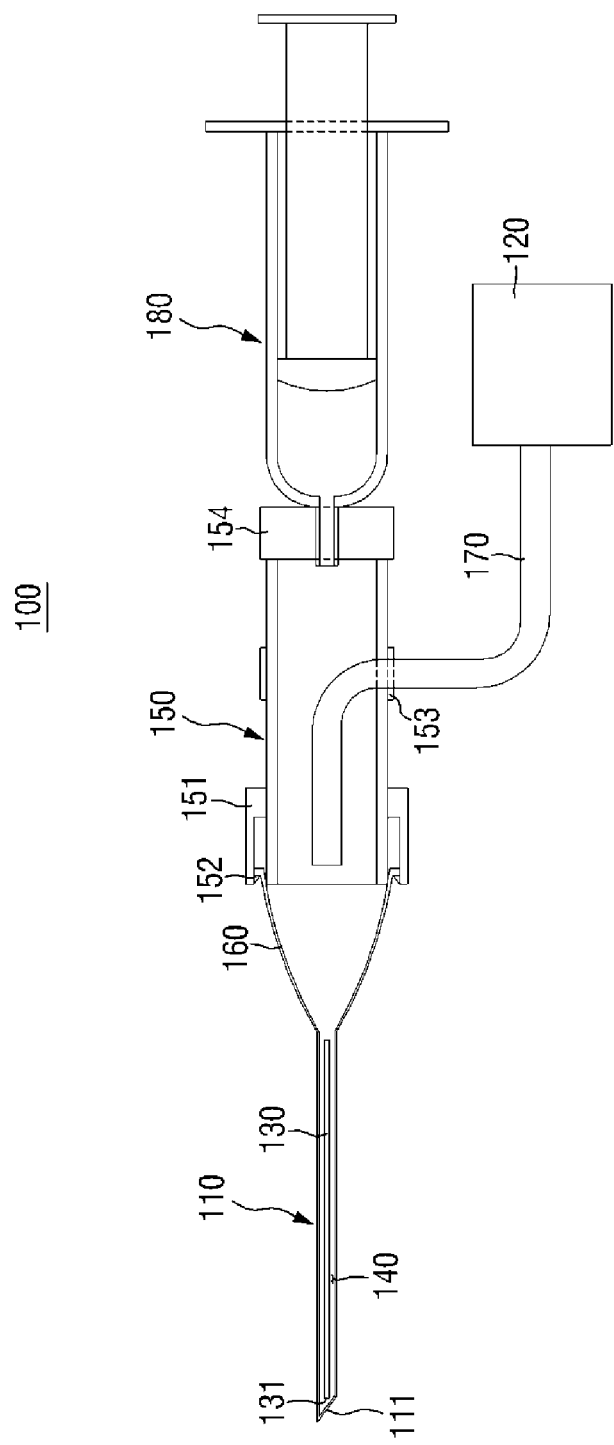
FIG. 2 is a sectional view of the optically induced injection device shown in FIG. 1.
Figure 3:
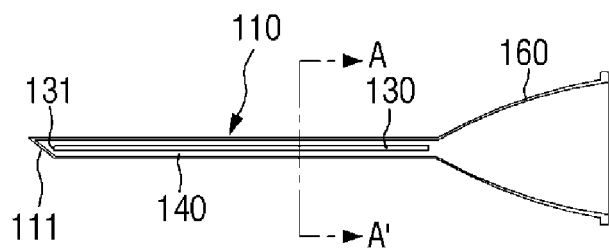
FIG. 3 is a sectional view of an injection needle according to an exemplary embodiment of the present disclosure.
Figure 4:
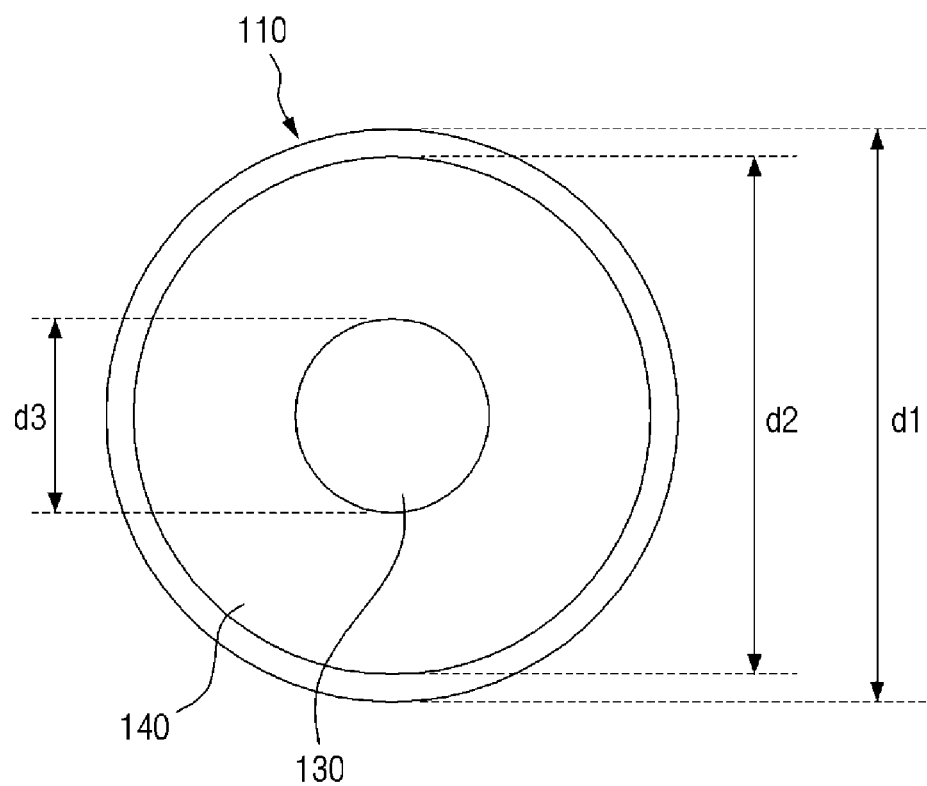
FIG. 4 is a sectional view taken along the line A-A' of FIG. 3.
Figure 5:
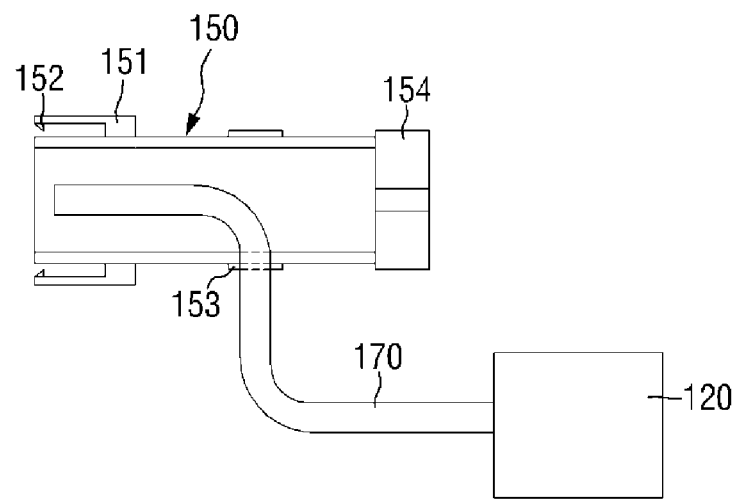
FIG. 5 is a sectional view of a body according to an exemplary embodiment of the present disclosure.

FIG. 1 is aperspective view of an optically induced injection device according to an exemplary embodiment of the present disclosure. FIG. 2 is a sectional view of the optically induced injection device shown in FIG. 1. FIG. 3 is a sectional view of an injection needle according to an exemplary embodiment of the present disclosure. FIG. 4 is a sectional view taken along the line A-A' of FIG. 3. FIG. 5 is a sectional view of a body according to an exemplary embodiment of the present disclosure.

Referring to FIG. 1 and FIG. 2, an optically induced injection device 100 may include an injection needle 110, a light generator 120, a first optical cable 130, an injection unit 140, a body 150, a fixing unit 151, a fixing pin 152, a second optical cable connector 153, a syringe connector 154, an injection needle connector 160, a second optical cable 170, and a syringe 180.

The injection needle 110 may be disposed at one end of the optically induced injection device 100. The injection needle 110 may include an injection needle tip 111 and an injection needle connector 160. Further, the injection needle 110 may include the first optical cable 130 and the injection unit 140 therein.

Referring to FIG. 4, the outer diameter d1 of the injection needle 110 may be 0.305 mm (30 Gauge needle) to 1.270 mm (18 Gauge needle). Specifically, when the outer diameter d1 is smaller than 0.305 mm, the diameters of the first optical fiber 130 and injection unit 140 included in the injection needle 110 may be reduced. Thus, it may not be easy to observe the position of the injection needle tip 111 with an endoscope. In addition, when the viscosity of an injection solution is high, the injection of the injection solution may not be easy. Therefore, the injection unit 140 cannot efficiently supply the injection solution to the affected area of a patient. In addition, when the diameter of the first optical cable 130 disposed in the injection needle 110 becomes smaller, light cannot be efficiently applied to the affected area of the patient. However, the present disclosure is not limited thereto. That is, in some other embodiments, the outer diameter d1 of the injection needle 110 may be smaller than 0.305 mm.

Further, specifically, when the outer diameter d1 is larger than 1.270 mm, a possibility of damage or bleeding of surrounding tissues of the affected area of the patient may increase. However, the present disclosure is not limited thereto. That is, in some other embodiments, the outer diameter d1 of the injection needle 110 may be larger than 1.270 mm.

Referring to FIG. 4, the inner diameter d2 of the injection needle 110 may be 0.140 mm (30 Gauge needle) to 0.838 mm (18 Gauge needle). Specifically, when the inner diameter d2 is smaller than 0.140 mm, the diameters of the first optical fiber 130 and injection unit 140 included in the injection needle 110 may be reduced. Thus, as described above, the injection solution and light cannot be efficiently supplied to the affected area of the patient. However, the present disclosure is not limited thereto. That is, in some other embodiments, the inner diameter d2 of the injection needle 110 may be smaller than 0.140 mm.

Further, specifically, when the inner diameter d2 of the injection needle 110 is larger than 0.838 mm, a possibility of damage or bleeding of surrounding tissues of the affected area of the patient may increase due to the increase of the outer diameter. However, the present disclosure is not limited thereto. That is, in some other embodiments, the inner diameter d2 of the injection needle 110 may be larger than 0.838 mm.

The injection needle 110 may be inserted into the affected area of the patient to provide the light and the injection solution to the affected area thereof. Specifically, the injection needle 110 may supply the injection solution to the affected area of the patient while applying light to the affected part thereof. However, the present disclosure is not limited thereto. That is, in some other embodiments, the light and the injection solution may be provided separately.

The injection needle tip 111 may be disposed at one end of the injection needle 110. The injection needle tip 111 may be formed to have a sharp end, so that the injection needle 110 can be easily inserted into the skin of the patient.

The injection needle connector 160 may be disposed at the other end of the injection needle 110 corresponding to one end of the injection needle 110. The injection needle connector 160 may have a shape that increases in diameter as it is away from the injection needle 110. Thus, the injection needle connector 160 can easily provide the light and injection solution supplied from the body 150 to the injection needle 110.

The injection needle connector 160 may be connected with the body 150. The portion where the injection needle connector 160 is connected with the body 150 may be formed to protrude from the lateral surface of the injection needle connector 160. Such a protrusion may be engaged with the body 150 by the fixing unit 150.

The injection needle connector 160 may be detached from the body 150. Thus, the injection needle 110 may be used as a disposable injection needle, and the economical efficiency of the optically induced injection device 100 can be improved.

The injection needle connector 160 may reflect the light provided from the body 150 to the inside of the injection needle connector, so that the light provided from the body 150 may be provided to the injection needle 110.

The first optical cable 130 may be disposed in a predetermined regionof the injection needle 110. For example, as shown in FIG. 4, the first optical cable 130 may be disposed in the center of the injection needle 110. However, the present disclosure is not limited thereto. That is, in some other embodiments, the first optical cable 130 may be disposed to be in contact with the inner side wall of the injection needle 110. Further, in some other embodiments, the first optical cable 130 may be disposed outside the injection needle 110.

Referring to FIG. 4, the diameter d3 of the first optical cable 130 may be 10 μm to 200 μm. Specifically, when the diameter d3 of the first optical cable 130 is smaller than 10 μm, light may not be transmitted easily. Further, when the diameter d3 of the first optical cable 130 is larger than 200 μm, the area of the first optical cable 130 occupying the inside of the injection needle 110 increases. Thus, there may be a disadvantage of an injection needle 110 having a large diameter being used or the area of the injection unit 140 occupying the inside of the injection needle 110 being relatively decreased.

The first optical cable 130 may include a core, a clad, and a jacket. The core may be an optical fiber made of very thin glass or plastic. The clad may be a Kevlar fiber for protecting the optical fiber. The clad may not be disturbed by an external current as a light pulse of the optical fiber, and may include glass or plastic having different optical properties from the core. The jacket, which is the outermost layer of an optical fiber bundle, may include a plastic material, and can protect the first optical cable 130 from moisture, abrasion, or damage.

The first optical cable 130 may totally reflect the light provided from the body 150 to the inside of the first optical cable 130, so that the light can be easily provided to the affected area of the patient.

The first optical cable 130 may include a first optical cableterminal 131 disposed at a position corresponding to that of the injection needle tip 111. As shown in FIG. 3, the injection needle tip 111 may further protrude compared to the first optical cable terminal 131. Thus, when inserting the injection needle tip 111 into the affected area of the patient, the injection needle tip 111 can be easily inserted into the affected area of the patient without being disturbed by the first optical cable terminal 131.

The injection unit 140 may be disposed in the remaining region of the inside of the injection needle 110 except for the first optical cable 130. For example, as shown in FIG. 4, the injection unit 140 may be disposed between the first optical cable 130 and the injection needle 110. However, the present disclosure is not limited thereto. That is, in some other embodiments, the injection unit 140 may be disposed within the injection needle 110 in a certain region that is independent of the first optical cable 130.

The injection unit 140 may provide the injection solution provided from the body 150 to the affected area of the patient. In this case, the injection unit 140 may provide the injection solution to the affected area of the patient while applying light to the affected area of the patient. However, the present disclosure is not limited thereto. That is, in some other embodiments, the light and the injection solution may be provided separately.

Referring to FIG. 5, the body 150 may include a fixing unit 151, a fixing pin 152, a second optical cable connector 153, and a syringe connector 154.

The body may be hollow such that the injection solution can move. The body may connect an injection needle connector 160, a syringe 180, and a light generator 120.

The body 150 may include a part of a second optical cable 170 therein. However, the present disclosure is not limited thereto. That is, in some other embodiments, the second optical cable 170 may not be disposed in the body 150.

The fixing unit 151 may be disposed to surround a part of the body 150 engaged with the injection needle connector 160. A part of the fixing unit 151 may be disposed to be in contact with the body 150. The fixing unit 151 may be engaged with the injection needle connector 160 to fix the injection needle 110 to the body 150.

The injection needle 110 may be detached from the body 150 by the fixing unit 151 and the injection needle connector 160. Thus, the injection needle 110 may be used as a disposable injection needle.

The fixing pin 152 may be disposed at one end of a portion where the fixing pin 152 is engaged with the injection needle connector 160. The fixing pin 152 may be disposed to protrude toward the body 150 from a portion where the fixing unit 151 is spaced apart from the body 150.

When the body 150 is engaged with the injection needle connector 160, the fixing pin 152 may be engaged with the protrusion disposed at one end of the injection needle connector 160 to fix the injection nozzle connector 160 to the body 150. Further, when the fixing pin 152 is spaced apart from the injection nozzle connector 160, the injection nozzle connector 160 may be detached from the body 150. Thus, the injection needle 110 may be detached from the body 150.

The second optical cable connector 153 may be disposed to surround a part of the lateral surface of the body 150. The second optical cable connector 153 may connect the second optical cable 170 and the body 150, and may fix the second optical cable 170 to the body 150.

The syringe connector 154 may be disposed at one end of the body 150. Specifically, the syringe connector 154 may be disposed at the other end of the body 150 corresponding to one end of the body 150 at which the fixing unit 151 is disposed.

The syringe connector 154 may include an opening in a direction in which the body extends. Through this opening, the syringe connector 154 may be engaged with the syringe 180, and the injection solution supplied from the syringe may be introduced into the body 150.

The syringe connector 154 may detach the syringe 180 from the body 150. Thus, the syringe 180 can be used as a disposable syringe, and the economical efficiency of the optically induced injection device 100 can be improved.

The light generator 120 may be disposed outside the body 150. The position of the light generator 120 is not specified, and the light generator 120 may be disposed to be spaced apart from the body 150. However, the present disclosure is not limited thereto. That is, in some other embodiments, the light generator 120 may be directly connected with the body 150.

The light generator 120 may generate light, and may provide the light to the body 150. Specifically, the light generator 120 of the optically induced injection device according to the present disclosure may employ a laser generator. When a laser is used as light, even if an optical cable having a small diameter is used, light can be effectively transmitted to the terminal of the optical cable, and thus this case can be advantageous in the procedure. However, the present disclosure is not limited thereto. That is, in some other embodiments, the light generator 120 may be at least one of a halogen lamp, a xenon lamp, and a light-emitting diode.

The second optical cable 170 may connect the second optical cable connector 153 and the light generator 120. The second optical cable 170 may provide the light generated by the light generator 120 to the inside of the body 150.

The second optical cable 170 may include a core, a clad, and a jacket. The core may be an optical fiber made of very thin glass or plastic. The clad may be a Kevlar fiber for protecting the optical fiber. The clad may not be disturbed by an external current as a light pulse of the optical fiber, and may include glass or plastic having different optical properties from the core. The jacket, which is the outermost layer of an optical fiber bundle, may include a plastic material, and can protect the second optical cable 170 from moisture, abrasion, or damage.

The diameter of the second optical cable 170, unlike the diameter of the first optical cable 130, may not be limited. However, since the second optical cable 170 should be connected to the second optical cable connector 153 disposed on the lateral surface of the body 150, the diameter of the second optical cable 170 may be determined in consideration of this circumstance.

In addition, since the second optical cable 170 should efficiently provide the light generated by the light generator 120 to the inside of the body 150, the diameter of the second optical cable 170 may be determined in consideration of this circumstance.

A part of the second optical cable 170 may be disposed inside the body 150. Specifically, the second optical cable 170 may be disposed to extend from the inside of the body 150 to a portion where the second optical cable 170 is engaged with the injection needle connector 160. Thus, light can be supplied to the injection needle 110 even if the inside of the body 150 does not reflect the light.

Although it is shown in FIG. 5 that the second optical cable 170 is disposed to be space apart from the inner side wall of the body 150, the present disclosure is not limited thereto. That is, in some other embodiments, the second optical cable 170 may disposed to be in contact with the inner side wall of the body 150.

The syringe 180 may be engaged with the syringe connector 154 disposed at one end of the body 150. As the syringe 180, a generally-used disposable syringe may be used. Therefore, the economical efficiency of the optically induced injection device 100 can be improved.

Hereinafter, a procedure of transcutaneous vocal fold injection using the optically induced injection device according to some exemplary embodiments of the present disclosure and advantages of the optically induced injection device according to the present disclosure will be described with reference to FIG. 6.

Figure 6:
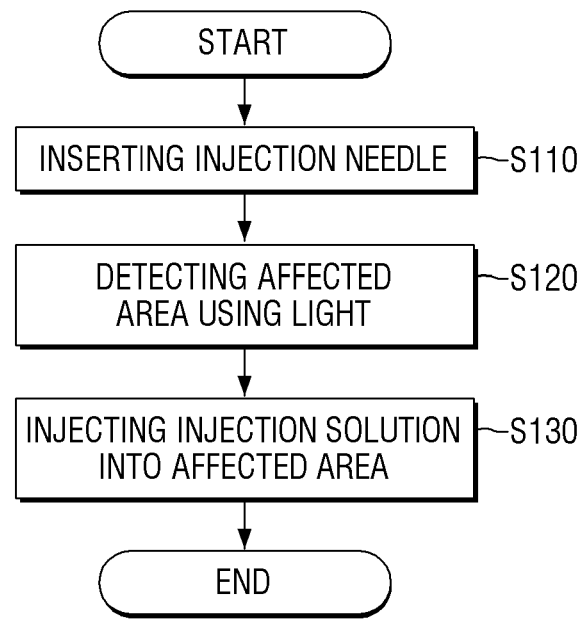
FIG. 6 is a flowchart sequentially showing a procedure of transcutaneous vocal fold injection using the optically induced injection device according to some exemplary embodiments of the present disclosure.

FIG. 6 is a flowchart sequentially showing a procedure of transcutaneous vocal fold injection using the optically induced injection device according to some exemplary embodiments of the present disclosure.

Referring to FIG. 6, a practitioner may insert the injection needle 110 of the optically induced injection device 100 into the external skin of the vocal folds of a patient (S110). As the anesthesia performed before inserting the injection needle 110, local anesthesia such as skin anesthesia and anesthesia for inserting an endoscope may be used. The practitioner may insert an endoscope for monitoring the procedure into the oral cavity.

The practitioner may detect the targeted affected area of the patient using the light provided through the first optical cable 130 in the needle 110 (S120). Thus, the practitioner may detect the position of the injection needle tip 111 without an additional light source. In this case, it is possible to reduce the damage of the internal tissues of the patient by using a light source with low heat generation.

After the practitioner detects the targeted affected area of the patient using the light, the practitioner may insert the injection needle tip 111 into the targeted affected area of the patient while maintaining the light irradiation. Subsequently, the practitioner may inject the injection solution into the affected area (S130). In this case, the process of irradiating the affected area with light and the process of injecting the injection solution into the affected area may be performed at the same time. However, the present disclosure is not limited thereto. That is, in some other embodiments, the light and the injection solution may be provided separately.

When the practitioner re-injects the injection solution into the same affected area during the procedure, the practitioner may re-inject the injection solution into the targeted affected area of the patient according to the above-described procedure.

When the optically induced injection device 100 according to the present disclosure is used, the procedure may be performed only by local anesthesia instead of general anesthesia. Further, in this case, compared with transoral injection, the procedure can be performed even by a general injection needle having a length of about 3 cm, and the injection solution can be accurately injected into the targeted affected area of the patient, so as to reduce side effects, such as laryngeal convulsion, lidocaine toxicity, inhalation due to bleeding, and vasovagal syncope. In addition, the procedure time and the anesthesia time can be reduced, the compliance of the patient can be improved, and the incidence of complications can be reduced.

Due to these advantages, when using the optically induced injection device according to the present disclosure, vocal fold injection can be effectively performed in the outpatient treatment of the patient.

Since the transcutaneous vocal fold injection is configured to inject the injection solution submucosally or intramuscularly without passing through the laryngeal mucosa, there is less possibility of laryngeal reflex and laryngospasm in comparison with transoral injection, so that, recently, this transcutaneous vocal fold injection has been increasingly used. As the representative method of the transcutaneous vocal fold injection, there is a trans-cricothyroid membrane approach. In this case, unlike the transoral injection in which the injection solution is injected while seeing the tip of the injection needle, the position of the injection needle is observed while moving the injection needle, and thus relatively thick injection needles (24 to 25 gauges) may be used.

The transcutaneous vocal fold injection, similarly to the transoral injection, may not need the anesthesia of vocal folds or epiglottises, and may also not need the administration of a sedative. The procedure assistant should show the vocal folds to the practitioner through stiff laryngoscope or flexural laryngoscope, and the practitioner can perform the procedure beside the patient. The injection needle having passed through a trans-cricothyroid membrane may move into glottis-adjacent tissues. When the injection needle protrudes into airway mucosa, the injection needle may be repositioned, and then the procedure may be performed again.

Since the lower part of glottis in anterior commissure does not have any glottis-adjacent tissue, it should be noted that the injection needle penetrates the airway mucosa when the injection needle is inserted into the midline. The practitioner may move the optically induced injection device left and right and up and down while observing the vocal folds of the patient through monitoring, so as to roughly gauge the position of the tip of the injection needle in the vocal folds.

Transcutaneous vocal fold injection may have advantages such as short procedure time, procedure stability, and easiness of outpatient procedure, as compared with transoral injection. Transcutaneous vocal fold injection is not a procedure performed while seeing the tip of the injection needle at the time of injecting the injection solution, as compared with transoral injection. Therefore, the accurate position of the tip of the injection needle can be detected using the motion of mucosa by moving the injection needle.

In vocal fold injection, the microstructure of vocal folds that need to be targeted may be changed depending on disease and drug. For example, in the case of vocal fold paralysis, intramuscular injection may be required in order not to make an influence on mucosal vibration while expanding the sufficient volume of vocal folds. In the case of vocal fold nodule or vocal fold blister, a drug should be directly injected submucosally due to mucosal lesion.

Hereinafter, an optically induced injection device according to another exemplary embodiment of the present disclosure will be described with reference to FIG. 7 to FIG. 9. Differences from the exemplary embodiment of FIG. 1 will be mainly described.

Figure 7:
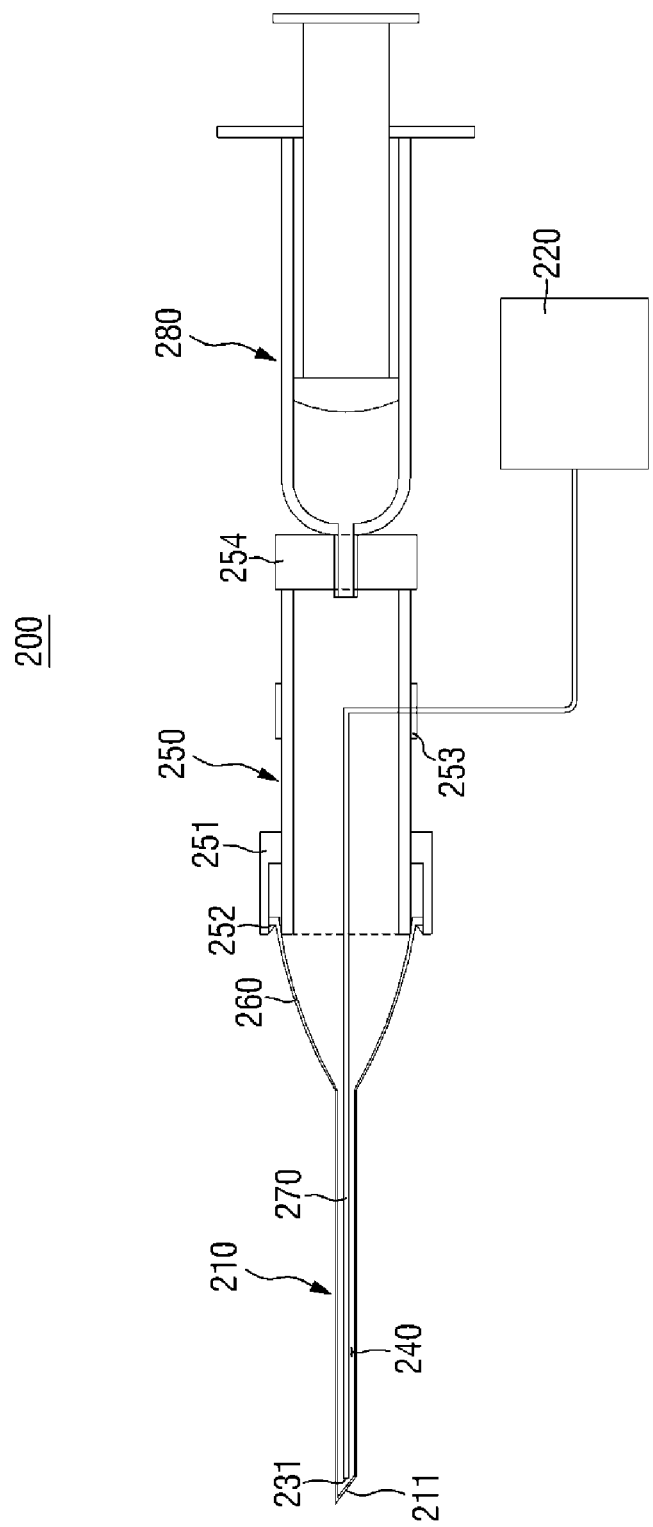
FIG. 7 is a sectional view of an optically induced injection device according to another exemplary embodiment of the present disclosure.

FIG. 7 is a sectional view of an optically induced injection device according to another exemplary embodiment of the present disclosure. FIG. 8 is a sectional view of an injection needle according to another exemplary embodiment of the present disclosure. FIG. 9 is a sectional view of a body according to another exemplary embodiment of the present disclosure.

Referring to FIG. 7, an optically induced injection device 200 may include an injection needle 210, a light generator 220, an injection unit 240, a body 250, a fixing unit 251, a fixing pin 252, an optical cable connector 253, a syringe connector 254, an injection needle connector 260, an optical cable 270, and a syringe 280.

The optically induced injection device 200, unlike the optically induced injection device 100, may include one optical cable 270. Specifically, unlike in the case of the first and second optical fibers 130 and 170 of the optically induced injection device 100 being separated and spaced from each other, the optical cable 270 may be formed integrally. More specifically, the optical cable 270 connecting the light generator 220 and the optical cable connector 253 may be disposed to extend continuously in the body 250, the injection needle connector 260 and the injection needle 210.

The optical cable 230 may include an optical cable terminal 231 disposed at the position corresponding to an injection needle tip 211. As shown in FIG. 7, the injection needle tip 211 may further protrude compared to the optical cable terminal 231. Thus, when inserting the injection needle tip 211 into the affected area of the patient, the injection needle tip 211 can be easily inserted into the affected area of the patient without being disturbed by the optical cable terminal 231.

Figure 8:
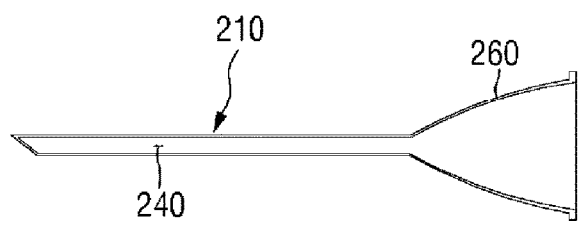
FIG. 8 is a sectional view of an injection needle according to another exemplary embodiment of the present disclosure.

Referring to FIG. 8, it can be seen that the injection needle 210 includes the injection unit 240 and the injection needle connector 260 except for the optical cable 270.

Figure 9:
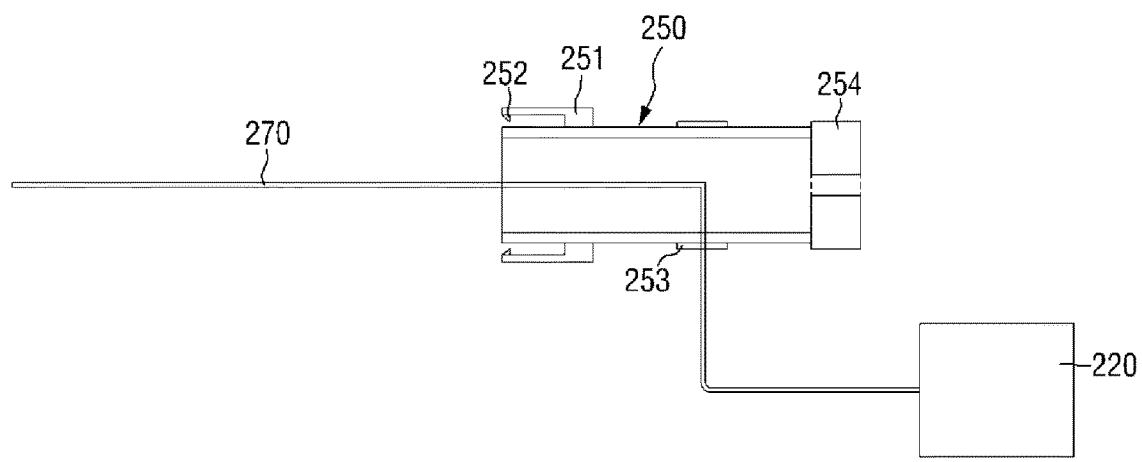
FIG. 9 is a sectional view of a body according to another exemplary embodiment of the present disclosure.

Referring to FIG. 9, unlike the optically induced injection device 100, the optical cable 270 may be connected with the body 250, so that, when the injection needle 210 is detached, only the remaining portion of the injection needle 270, except for the optical cable 270, may be detached.

Since the optically induced injection device 200, unlike the optically induced injection device 100, may use the injection needle 210 not including the first optical cable 130, there is an advantage of reducing the cost of a disposable injection needle.

Hereinafter, an optically induced injection device according to still another exemplary embodiment of the present disclosure will be described with reference to FIG. 10 and FIG. 11. Differences from the exemplary embodiment of FIG. 1 will be mainly described.

Figure 10:
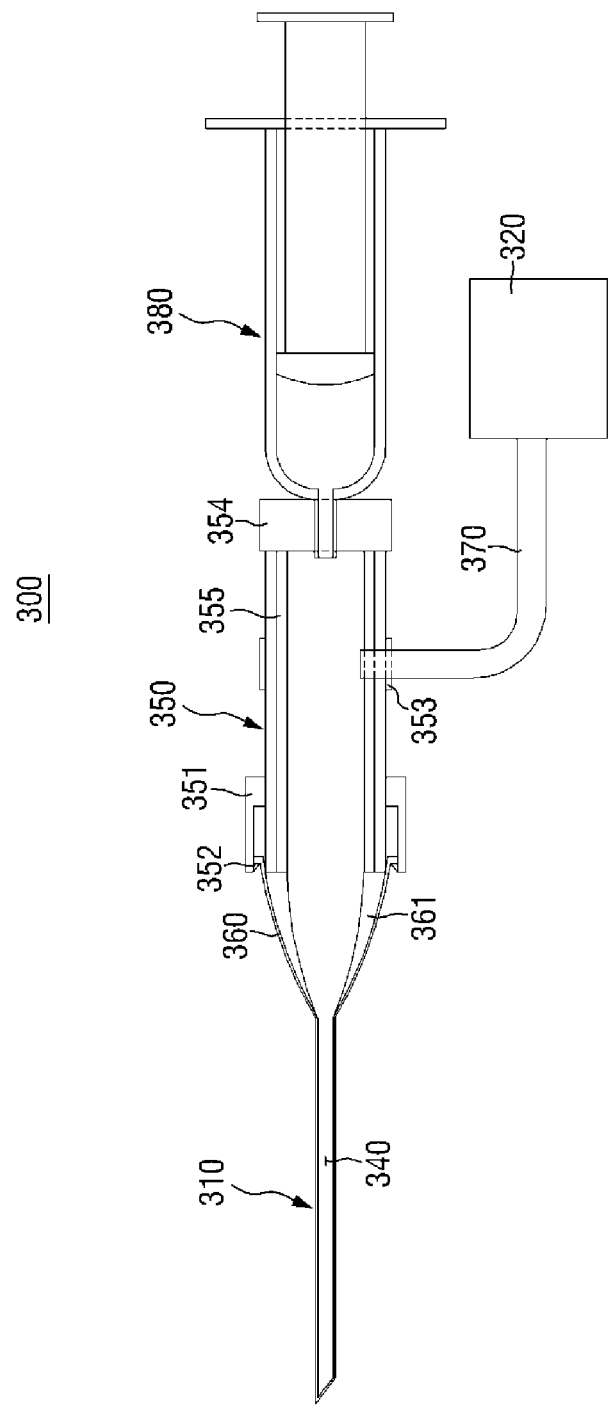
FIG. 10 is a sectional view of an optically induced injection device according to still another exemplary embodiment of the present disclosure.

FIG. 10 is a sectional view of an optically induced injection device according to still another exemplary embodiment of the present disclosure. FIG. 11 is a sectional view of an injection needle according to still another exemplary embodiment of the present disclosure.

Referring to FIG. 10, an optically induced injection device 300 may include an injection needle 310, a light generator 320, an injection unit 340, a body 350, a fixing unit 351, a fixing pin 352, an optical cable connector 353, a syringe connector 354, a total reflection coating film 355, an injection needle connector 360, a reflective film 361, an optical cable 370, and a syringe 380.

The optically induced injection device 300, unlike the optically induced injection device 100, may be configured such that the optical cable 370 is not disposed in the body 350, the needle connecting unit 360 and the injection needle 310.

Further, the optically induced injection device 300, unlike the optically induced injection device 100, may further include the total reflection coating film 355 in the body 350. The total reflection coating film 355 may be disposed to surround the inner side wall of the body 350.

The total reflection coating film 355 may totally reflect the light provided from the optical cable 370, so as to provide the light to the injection needle 310 even when an optical cable does not exist in the body 350. The injection needle 310 may reflect the light provided from the body 350 and provide this light to the affected area of the patient.

The optical cable 370 may be disposed to connect the light generator 320 and the optical cable connector 353 and to allow one end of the optical cable 370 to be exposed to the inside of the body 350.

Figure 11:
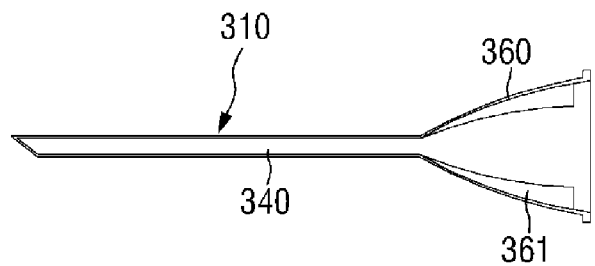
FIG. 11 is a sectional view of an injection needle according to still another exemplary embodiment of the present disclosure.

Referring to FIG. 11, the optically induced injection device 300, unlike the optically induced injection device 100, may further include the reflective film 361 in the injection needle connector 360. The reflective film 361 may be disposed to surround the inner side wall of the injection needle connector 360.

The reflective film 361 may totally reflect the light provided from the body 350, so as to provide the light to the injection needle 310 even when an optical cable does not exist in the injection needle connector 360.

Since the optically induced injection device 300, unlike the optically induced injection device 100, may use the injection needle 310 not including the first optical cable 130, there is an advantage of reducing the cost of a disposable injection needle. Further, since the optically induced injection device 300, unlike the optically induced injection device 200, does not include the optical cable 270 protruding toward the outside of the body 250, it is possible to reduce the disadvantage of the exposed optical cable 270 being damaged when the injection needle 210 is detached.

Hereinafter, an optically induced injection device according to still another exemplary embodiment of the present disclosure will be described with reference to FIG. 12. Differences from the exemplary embodiment of FIG. 1 will be mainly described.

Figure 12:
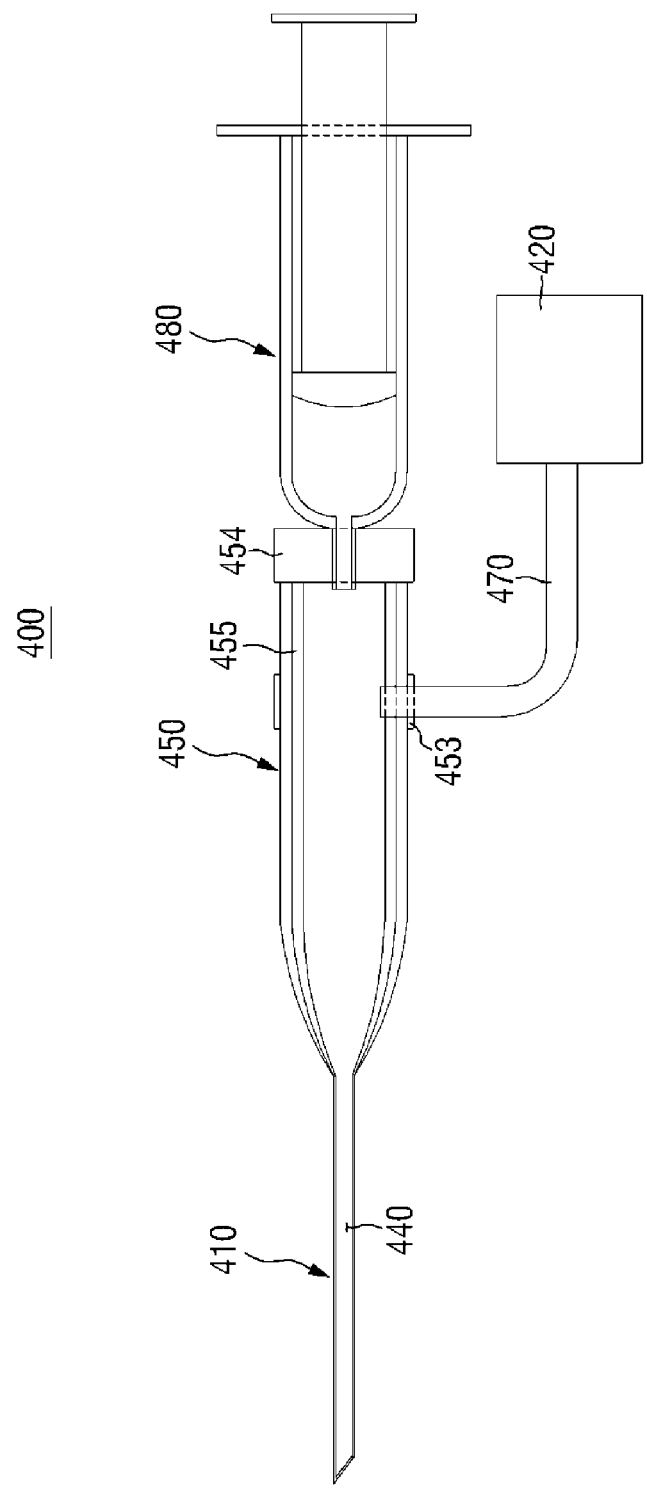
FIG. 12 is a sectional view of an optically induced injection device according to still another exemplary embodiment of the present disclosure.

FIG. 12 is a sectional view of an optically induced injection device according to still another exemplary embodiment of the present disclosure.

Referring to FIG. 12, an optically induced injection device 400 may include an injection needle 410, a light generator 420, an injection unit 440, a body 450, an optical cable connector 453, a syringe connector 454, a total reflection coating film 455, an optical cable 470, and a syringe 480.

The optically induced injection device 400, unlike the optically induced injection device 100, may be configured such that the optical cable 470 is not disposed in the body 450 and the injection needle 410. Further, the optically induced injection device 400, unlike the optically induced injection device 100, maynot the fixing unit 151, the fixing pin 152, and the injection needle connector 160. Specifically, the optically induced injection device 400 may be configured such that the injection needle 410 and the body 450 are integrally formed. That is, it is impossible to detach the injection needle 410 and the body 450 from each other.

Further, the optically induced injection device 400, unlike the optically induced injection device 100, may further include the total reflection coating film 455 in the body 450. The total reflection coating film 455 may be disposed to surround the inner side wall of the body 450.

The total reflection coating film 455 may totally reflect the light provided from the optical cable 470, so as to provide the light to the injection needle 410 even when an optical cable does not exist in the body 450. The injection needle 410 may reflect the light provided from the body 450 and provide this light to the affected area of the patient.

The optical cable 470 may be disposed to connect the light generator 420 and the optical cable connector 453 and to allow one end of the optical cable 470 to be exposed to the inside of the body 450.

Hereinafter, an optically induced injection device according to still another exemplary embodiment of the present disclosure will be described with reference to FIG. 13. Differences from the exemplary embodiment of FIG. 1 will be mainly described.

Figure 13:
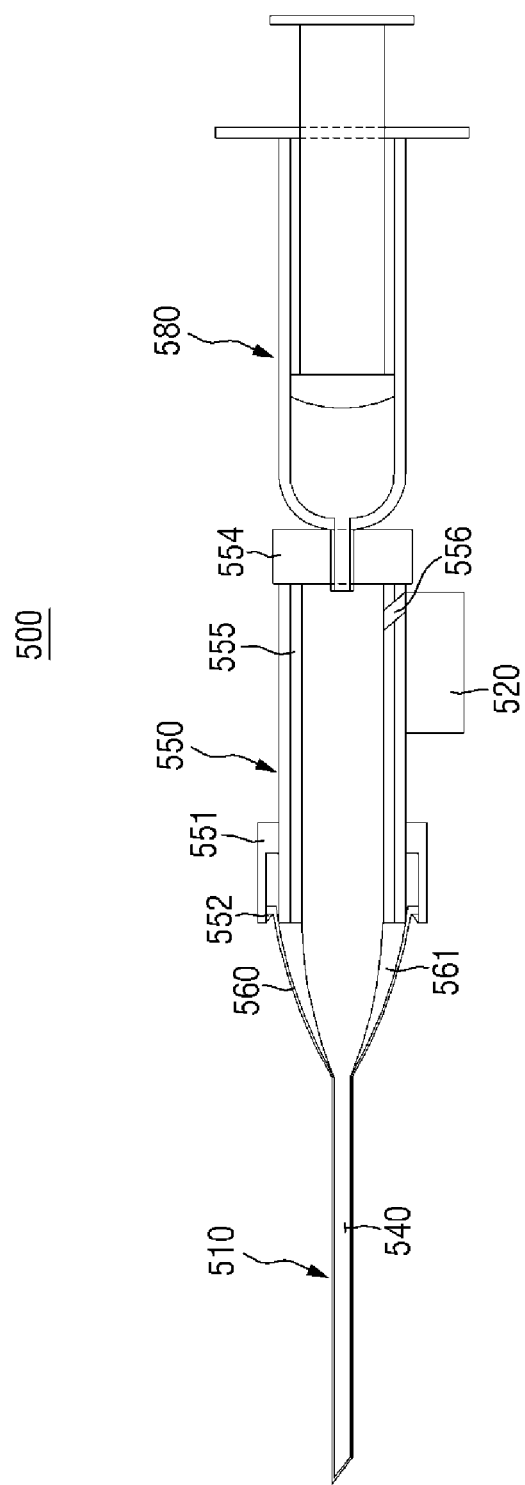
FIG. 13 is a sectional view of an optically induced injection device according to still another exemplary embodiment of the present disclosure.

FIG. 13 is a sectional view of an optically induced injection device according to still another exemplary embodiment of the present disclosure.

Referring to FIG. 13, an optically induced injection device 500 may include an injection needle 510, a light generator 520, an injection unit 540, a body 550, a fixing unit 551, a fixing pin 552, a syringe connector 554, a total reflection coating film 555, a light-transmitting film 556, an injection needle connector 560, a reflective film 561, and a syringe 580.

The optically induced injection device 500, unlike the optically induced injection device 100, may not include the first and second optical cables 130 and 170. Specifically, an optical cable may not be disposed in the body 550, the injection needle connector 560, and the injection needle 510. Further, the light generator 520 may be directly connected with the body 550.

The light generator 520 may be disposed on the lateral surface of the body 550, and may be connected with the inside of the body 550 through the light-transmitting film 556.

The light-transmitting film 556 may be disposed to penetrate the lateral surface of the body 550. The light generated from the light generator 520 may be provided into the body 550 through the light-transmitting film 556. The light-transmitting film 556 may serve to prevent the injection solution in the body 550 from being introduced into the light generator 520.

The optically induced injection device 500, unlike the optically induced injection device 100, may further include the total reflection coating film 555 in the body 550. The total reflection coating film 555 may be disposed to surround the inner side wall of the body 550.

Further, the optically induced injection device 500 may further include the reflective film 561 in the injection needle connector 560. The reflective film 561 may be disposed to surround the inner side wall of the injection needle connector 560.

Since the optically induced injection device 500, unlike the optically induced injection device 100, may use the injection needle 510 not including the first optical cable 130, there is an advantage of reducing the cost of a disposable injection needle. Further, since the optically induced injection device 500 does not include an optical cable connecting the light generator 520 with the body 550, and allows the light generator 520 to be disposed on the lateral surface of the body 550, thereby simplifying the structure of the optically induced injection device 500.

Hereinafter, an optically induced injection device according to still another exemplary embodiment of the present disclosure will be described with reference to FIG. 14. Differences from the exemplary embodiment of FIG. 1 will be mainly described.

Figure 14:
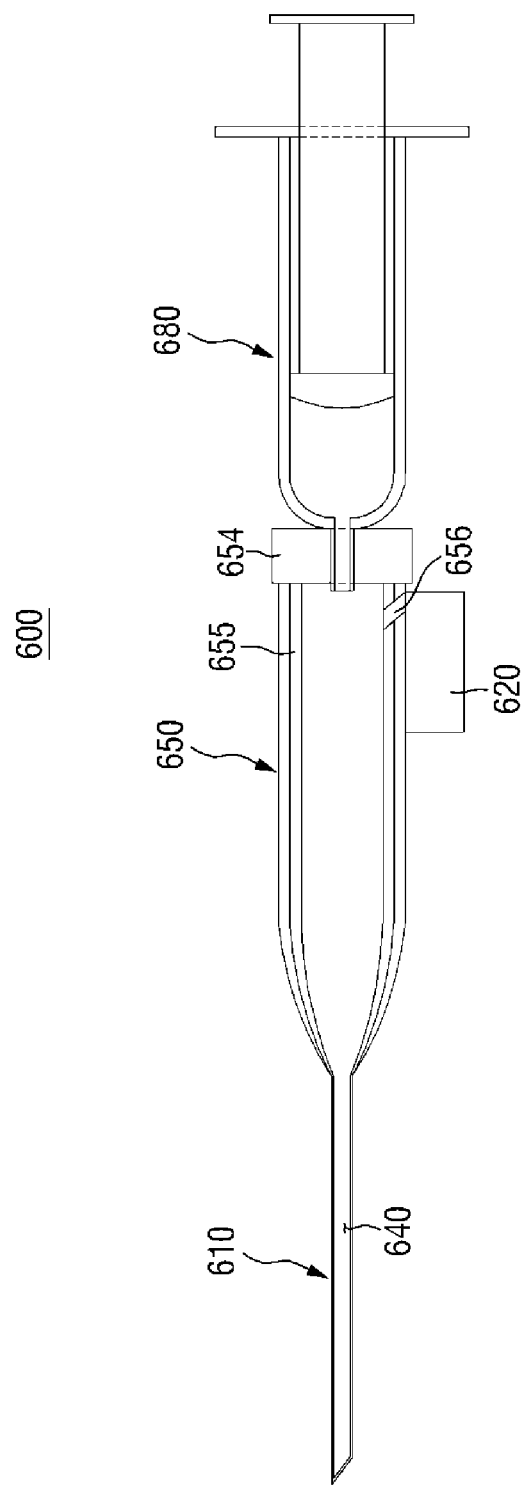
FIG. 14 is a sectional view of an optically induced injection device according to still another exemplary embodiment of the present disclosure.

FIG. 14 is a sectional view of an optically induced injection device according to still another exemplary embodiment of the present disclosure.

Referring to FIG. 14, an optically induced injection device 600 may include an injection needle 610, a light generator 620, an injection unit 640, a body 650, a syringe connector 654, a total reflection coating film 655, a light-transmitting film 656, and a syringe 680.

The optically induced injection device 600, unlike the optically induced injection device 100, may not include the first and second optical cables 130 and 170. Specifically, an optical cable may not be disposed in the body 650 and the injection needle 610. Further, the optically induced injection device 600 may not the fixing unit 151, the fixing pin 152, and the injection needle connector 160. Specifically, the optically induced injection device 600 may be configured such that the injection needle 610 and the body 650 are integrally formed. That is, it is impossible to detach the injection needle 610 and the body 650 from each other.

The light generator 620 may be disposed on the lateral surface of the body 650 to be directly connected with the body 650. The light generator 620 may be connected with the inside of the body 650 through the light-transmitting film 656. The light-transmitting film 656 may be disposed to penetrate the lateral surface of the body 650.

Further, the optically induced injection device 600, unlike the optically induced injection device 100, may further include the total reflection coating film 655 in the body 650. The total reflection coating film 655 may be disposed to surround the inner side wall of the body 650.

Although preferred exemplary embodiments of the present disclosure have been described for illustrative purposes, those skilled in the art will appreciate that various modifications, additions and substitutions are possible, without departing from the scope and spirit of the disclosure as disclosed in the accompanying claims.

What is claimed is:
1. An optically induced injection device, comprising:
an injection needle;
a light generator providing light to an affected area;
a body connecting the injection needle and the light generator;
a first optical cable which is disposed in the injection needle and through which the light passes;
a second optical cable connecting the light generator and the body and providing the light generated from the light generator to the first optical cable in the body; and
an injection unit disposed in the injection needle and providing an injection solution to the affected area while the light is provided to the affected area, wherein the first optical cable and the second optical cable are disposed to be spaced apart from each other in the body.

2. The optically induced injection device of claim 1, wherein the injection needle has an outer diameter of 0.305 mm to 1.270 mm.

3. The optically induced injection device of claim 1, wherein the injection needle has an inner diameter of 0.140 mm to 0.838 mm.

4. The optically induced injection device of claim 3, wherein the first optical cable has a diameter of 10 mm to 200 mm.

5. The optically induced injection device of claim 1, wherein an injection needle tip formed at one end of the injection needle further protrudes compared to a first optical cable terminal formed at a position corresponding to the one end of the injection needle.

6. The optically induced injection device of claim 1, further comprising: an injection needle connector disposed to the other end of the injection needle and connecting the injection needle and the body, wherein the injection needle connector is detachable from the body.

7. The optically induced injection device of claim 6, further comprising: a reflective film disposed the injection needle connector and reflecting the light into the injection needle.

8. The optically induced injection device of claim 6, further comprising: a fixing unit disposed the body and fixing the injection needle connector to the body.

9. An optically induced injection device, comprising:
a body;
a light generator connected with the body and providing light to the body;
a syringe connected with the body and providing an injection solution to the body;

an injection needle connected with the body and providing the injection solution to an affected area while the light is provided to the affected area;

a first optical cable which is disposed in the injection needle and through which the light passes; and a second optical cable connecting the light generator and the body and providing the light generated from the light generator to the first optical cable in the body, wherein the first optical cable and the second optical cable are disposed to be spaced apart from each other in the body.

10. The optically induced injection device of claim 9, wherein the light is a laser.

11. The optically induced injection device of claim 9, wherein the body reflects the light into the body.

12. The optically induced injection device of claim 11, further comprising: a total reflection coating film disposed the body to totally reflect the light.

13. The optically induced injection device of claim 11, wherein the light generator is disposed the body, and the light is applied into the body.

14. The optically induced injection device of claim 13, further comprising: a light-transmitting film covering an opening through which the light is applied.

15. The optically induced injection device of claim 9, wherein the injection needle reflects the light into the injection needle.

16. The optically induced injection device of claim 9, further comprising: a syringe connector connecting the body and the syringe, wherein the syringe is detachable from the syringe connector.

* * * * *

UNITED STATES PATENT AND TRADEMARK OFFICE
CERTIFICATE OF CORRECTION

PATENT NO. : 10,342,931 B2  
APPLICATION NO. : 15/536419  
DATED : July 9, 2019  
INVENTOR(S) : Wonjae Cha Page 1 of 1

It is certified that error appears in the above-identified patent and that said Letters Patent is hereby corrected as shown below:

In the Claims

In Claim 4, at Column 14, Lines 43 and 44:
Delete the text "10 mm to 200 mm" and replace it with the text --10 μm to 200 μm--.

Signed and Sealed this  
Eighth Day of October, 2019

Andrei Iancu  
*Director of the United States Patent and Trademark Office*